(12) United States Patent
Rodriguez et al.

(10) Patent No.: US 8,026,219 B2
(45) Date of Patent: Sep. 27, 2011

(54) ANTIMICROBIAL LINEAR PEPTIDES

(75) Inventors: Eduard Bardaji Rodriguez, Girona (ES); Emili Montesinos Segui, Girona (ES); Esther Badosa Romacho, Girona (ES); Lidia Feliu Soley, Girona (ES); Marta Planas Grabuleda, Girona (ES); Rafael Ferre Malagón, Girona (ES)

(73) Assignee: Universitat de Girona, Girona (ES)

( * ) Notice: Subject to any disclaimer, the term of this patent is extended or adjusted under 35 U.S.C. 154(b) by 558 days.

(21) Appl. No.: 12/298,580

(22) PCT Filed: Apr. 24, 2007

(86) PCT No.: PCT/ES2007/000244
§ 371 (c)(1), (2), (4) Date: Oct. 27, 2008

(87) PCT Pub. No.: WO2007/125142
PCT Pub. Date: Nov. 8, 2007

(65) Prior Publication Data
US 2010/0016167 A1    Jan. 21, 2010

(30) Foreign Application Priority Data
Apr. 28, 2006   (ES) .................................. 200601098

(51) Int. Cl.
*C07K 4/00*   (2006.01)

(52) U.S. Cl. .......... 514/21.6; 514/2.2; 530/327
(58) Field of Classification Search ........... None
See application file for complete search history.

(56) References Cited

FOREIGN PATENT DOCUMENTS
WO       WO03/008442    *   1/2003

OTHER PUBLICATIONS

Cavallarin et al. "Cecropin A—Derived Peptides Are Potent Inhibitors of Fungal Plant Pathogens." Molecular Plant-Microbe Interactions, vol. 11, No. 3, 1998, pp. 218-227.*

* cited by examiner

*Primary Examiner* — Anish Gupta
(74) *Attorney, Agent, or Firm* — Notaro, Michalos & Zaccaria P.C.

(57) ABSTRACT

The present invention relates to novel linear peptides with antimicrobial activity. Said peptides are made up of 11 amino acids, and they have the amino group of the amino acid constituting the N-terminal end in a non-derived form or functionalized with an acetyl group, p-toluene sulphonyl, benzyl or benzoyl. The amino acid constituting the C-terminal end of said peptides is in carboxamide form. The invention describes the synthesis and use of said peptides as antimicrobial agents to combat pathogenic bacteria for plants. The invention also relates to compositions containing said peptides and an auxiliary agent, and to a method for preventing and treating infections and diseases of plants caused by pathogenic bacteria.

23 Claims, No Drawings

ANTIMICROBIAL LINEAR PEPTIDES

FIELD OF THE INVENTION

The present invention relates to linear peptides with antimicrobial activity, which are particularly effective to combat pathogenic bacteria for plants, and that can be used in phytosanitary compositions.

PRIOR ART

Phytopathogenic bacteria are responsible for losses of great economic importance in plant production. Among them, we can highlight, for example bacteriosis caused by *Erwinia amylovora, Pseudomonas syringae* and *Xanthomonas vesicatoria*.

Currently, in Europe, only some products are authorized for the protection of plants against bacterial diseases mainly based on cupric derivatives with an insufficient control efficacy.

Antibiotics, such as kasugamicyn or streptomycin, which until recent years were authorized in some countries, are currently not authorized in Europe. The antibiotics streptomycin and tetracycline are authorized in countries such as the USA, but in numerous cases the appearance of resistant strains of the pathogen which makes their use ineffective has become evident. In the case of mycosis caused by phytopathogenic fungi, although there are active material available, new fungicides are constantly required, partly due to the appearance of resistances with a certain frequency.

Furthermore, many of the most effective antibacterial compounds known remain in the environment which is not desirable.

In recent years, the preparation of new types of antibiotics which may affect resistance of bacteria has intensified. Among them, we can highlight compounds isolated from nature, for example, peptides, which are present in plants and animals, and some of which have antimicrobial properties.

Cecropins are antimicrobial peptides present in the haemolymph of the *Hyalaphora cecropia* butterfly as a response to a bacterial infection. In particular, cecropin A is a linear peptide formed by 37 amino acids, which has a potent lytic activity against Gram-positive and Gram-negative bacteria. Nevertheless, there is reticence to using it in phytosanitary applications given its high production cost, as it has a considerable length, and its low stability against protease degradation.

In Ali et al, Mol. Plant-Microbe Interact., 2000, 13, 847-859 describes an active peptide to combat some pathogenic bacteria of plants such as *Erwinia carotovora* subsp. *carotovora* and *Erwinia carotovora* subsp. *atroseptica*. It is a undecapeptide prepared for the first time by Cavallarin et al. Mol. Plant-Microbe Interact., 1998, 11, 218-227, which is formed by the sequence of amino acids Trp-Lys-Leu-Phe-Lys-Lys-Ile-Leu-Lys-Val-Leu, and that the amino acid of the C-terminal end has a carboxamide group. Said peptide is a hybrid peptide formed by fragments of the peptides of natural origin cecropin A and melittin. Specifically, it is constituted by amino acids 2-8 of cecropin A and 6-9 of melittin.

The application of said undecapeptide to combat other phytopathogenic bacteria such as *Erwinia amylovora, Xanthomonas vesicatoria* and *Pseudomonas syringae* has not been described, which are particularly relevant as they affect plants which are of great economic importance, and against which to date the methods used to combat them are rather ineffective.

Therefore, there is still the need to have new antimicrobial compounds that have good efficacy against pathogenic bacteria of plants, in particular, against the bacteria *Erwinia amylovora, Xanthomonas vesicatoria* and/or *Pseudomonas syringae*.

OBJECT OF THE INVENTION

The authors of the present invention have developed new peptides which are of easy preparation and have a high efficacy to inhibit the growth of pathogenic bacteria of plants, in addition to having low cytotoxicity in eukaryotic cells, and a good stability to degradation by proteases.

The object of the present invention is to provide linear peptides which have antimicrobial properties.

The object of the invention is also the use of said peptides as antimicrobial agents.

The object of the invention is also a phytosanitary composition which comprises the peptides of the invention and an auxiliary agent.

Another object of the invention is a method to prevent infections and disease of plants caused by bacteria.

DESCRIPTION OF THE INVENTION

Peptides

The object of the present invention is to provide linear peptides which respond to general formula (I):

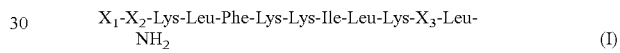

$$X_1\text{-}X_2\text{-Lys-Leu-Phe-Lys-Lys-Ile-Leu-Lys-}X_3\text{-Leu-NH}_2 \quad (I)$$

wherein $X_1$ is hydrogen, acetyl, p-toluene sulphonyl, benzyl or benzoyl, $X_2$ is Lys, Tyr, Leu, Phe, or Trp and $X_3$ is Lys, Tyr, Val, Phe or Trp, with the condition that the peptide wherein $X_1$ is hydrogen, $X_2$ is Trp and $X_3$ is Val is expressly excluded.

In the general formula, when $X_1$ is hydrogen it is represented as H, the acetyl group is represented by Ac, the p-toluene sulphonyl group as Ts, the benzyl group as Bn, and the benzoyl group as Bz.

The abbreviations used for the amino acids in this description follow the standards of the Commission on Biochemical Nomenclature of IUPAC-IUB, as described in the book Biochemical Nomenclature and Related Documents, $2^{nd}$ edition, Portland Press, 1992, London [ISBN 1-85578-005-4]. In this way, Leu is L-leucine, Lys means L-lysine, Ile is L-isoleucine, Phe is L-phenylalanine, Tyr is L-tyrosine, Trp is L-tryptophan and Val is L-valine.

In accordance with said standard, the peptides are represented with the abbreviations of the amino acids which compose them joined by dashes which represent the peptide bonds. Thus, for example, the peptide glycylglycylglycine is symbolized as Gly-Gly-Gly. This requires the modification of the symbol Gly for glycine, $H_2N\text{—}CH_2\text{—}COOH$, in three different forms:

(i) "Gly-" means $H_2N\text{—}CH_2\text{—}CO$
(ii) "-Gly-" means $HN\text{—}CH_2\text{—}CO\text{—}$, and
(iii) "-Gly" means $HN\text{—}CH_2\text{—}COOH$ Thus, when the dash is placed to the right of the symbol, case (i), it indicates that the OH group of the carboxylic group of the amino acid has been eliminated, and, when it is placed to the left of the symbol, case (iii), it indicates that a hydrogen atom has been eliminated from the amine group of the amino acid; in case (ii) both modifications are applied to the same symbol.

The amino acid Gly- constitutes the N-terminal end of the peptide, and the amino acid -Gly constitutes the C-terminal end of the peptide.

As can be appreciated from general formula (I), all peptides of the invention have the amino acid Leu of the C-terminal end of the carboxamide form, represented by -Leu-NH$_2$.

The amino acid which constitutes the N-terminal end of the peptides of the invention mainly maintain amino group non-derived, or it can be functionalized with an acetyl group, p-toluene sulphonyl, benzoyl or benzyl, as expressed in general formula (I).

In the case that said amine group is non-derived, i.e. when X$_1$ is hydrogen, in this description it is considered that the symbol H—X— is equivalent to the symbol X—, which is the form adopted by the IUPAC in the aforementioned case (i).

The structures of the peptides of the invention are defined in accordance with general formula (I).

Another form of defining the structure of the peptides of the invention consists of using the sequence of amino acids SEQ_ID_NO: 1 to SEQ_ID_NO: 25, and further specifying the functionalization they have at the N-terminal end and at the C-terminal end of the peptide. As has been indicated, all peptides of the invention have the amino acid which forms the C-terminal end in carboxamide form.

Said sequences have the amino acids shown in Table I:

TABLE I

| SEQ_ID_NO: | Structure |
|---|---|
| 1 | Lys-Lys-Leu-Phe-Lys-Lys-Ile-Leu-Lys-Lys-Leu |
| 2 | Tyr-Lys-Leu-Phe-Lys-Lys-Ile-Leu-Lys-Lys-Leu |
| 3 | Leu-Lys-Leu-Phe-Lys-Lys-Ile-Leu-Lys-Lys-Leu |
| 4 | Phe-Lys-Leu-Phe-Lys-Lys-Ile-Leu-Lys-Lys-Leu |
| 5 | Trp-Lys-Leu-Phe-Lys-Lys-Ile-Leu-Lys-Lys-Leu |
| 6 | Lys-Lys-Leu-Phe-Lys-Lys-Ile-Leu-Lys-Tyr-Leu |
| 7 | Tyr-Lys-Leu-Phe-Lys-Lys-Ile-Leu-Lys-Tyr-Leu |
| 8 | Leu-Lys-Leu-Phe-Lys-Lys-Ile-Leu-Lys-Tyr-Leu |
| 9 | Phe-Lys-Leu-Phe-Lys-Lys-Ile-Leu-Lys-Tyr-Leu |
| 10 | Trp-Lys-Leu-Phe-Lys-Lys-Ile-Leu-Lys-Tyr-Leu |
| 11 | Lys-Lys-Leu-Phe-Lys-Lys-Ile-Leu-Lys-Val-Leu |
| 12 | Tyr-Lys-Leu-Phe-Lys-Lys-Ile-Leu-Lys-Val-Leu |
| 13 | Leu-Lys-Leu-Phe-Lys-Lys-Ile-Leu-Lys-Val-Leu |
| 14 | Phe-Lys-Leu-Phe-Lys-Lys-Ile-Leu-Lys-Val-Leu |
| 15 | Trp-Lys-Leu-Phe-Lys-Lys-Ile-Leu-Lys-Val-Leu |
| 16 | Lys-Lys-Leu-Phe-Lys-Lys-Ile-Leu-Lys-Phe-Leu |
| 17 | Tyr-Lys-Leu-Phe-Lys-Lys-Ile-Leu-Lys-Phe-Leu |
| 18 | Leu-Lys-Leu-Phe-Lys-Lys-Ile-Leu-Lys-Phe-Leu |
| 19 | Phe-Lys-Leu-Phe-Lys-Lys-Ile-Leu-Lys-Phe-Leu |
| 20 | Trp-Lys-Leu-Phe-Lys-Lys-Ile-Leu-Lys-Phe-Leu |
| 21 | Lys-Lys-Leu-Phe-Lys-Lys-Ile-Leu-Lys-Trp-Leu |
| 22 | Tyr-Lys-Leu-Phe-Lys-Lys-Ile-Leu-Lys-Trp-Leu |
| 23 | Leu-Lys-Leu-Phe-Lys-Lys-Ile-Leu-Lys-Trp-Leu |
| 24 | Phe-Lys-Leu-Phe-Lys-Lys-Ile-Leu-Lys-Trp-Leu |
| 25 | Trp-Lys-Leu-Phe-Lys-Lys-Ile-Leu-Lys-Trp-Leu |

The sequence called SEQ_ID_NO:15 corresponds to the sequence of the peptide described by Cavallarin et al. Mol. Plant-Microbe Interact., 1998, 11, 218-227, whose carboxamide derivative at the C-terminal end of the sequence is expressly excluded from this invention.

Among the peptides of the invention which are preferred are the peptides defined by the sequences SEQ_ID_NO: 1 to SEQ_ID_NO: 14 and SEQ_ID_NO:16 to SEQ_ID_NO: 25, and which have the amino acid at the C-terminal end in the form of carboxamide group.

Within this group are particularly preferred the peptides defined by the sequences SEQ_ID_NO: 6 to SEQ_ID_NO: 11, SEQ_ID_NO: 13, SEQ_ID_NO: 16, SEQ_ID_NO: 18 to SEQ_ID_NO: 22 and SEQ_ID_NO: 25 and which have the amino acid at the C-terminal end in the form of carboxamide group.

Particularly preferred are the peptides defined by the sequences SEQ_ID_NO: 6 and SEQ_ID_NO: 16 and which have the amino acid of the C-terminal end in the form of carboxamide group. The last of these two preferred peptides has the structure: H-Lys-Lys-Leu-Phe-Lys-Lys-Ile-Leu-Lys-Phe-Leu-NH$_2$, corresponding to general formula (I) where X$_1$ is H, X$_2$ is Lys and X$_3$ is Phe.

Also preferred are the peptides defined by the sequences SEQ_ID_NO: 1 to SEQ_ID_NO: 25, and which have the amino acid of the N-terminal end functionalized with the acetyl group, and the amino acid of the C-terminal end in the form of carboxamide group.

Within this group especially preferred is the peptide defined by the sequence SEQ_ID_NO: 16, which has the amino acid of the N-terminal end functionalized with the acetyl group, and the amino acid of the C-terminal end in the form of carboxamide group. Said peptide has the structure Ac-Lys-Lys-Leu-Phe-Lys-Lys-Ile-Leu-Lys-Phe-Leu-NH$_2$, corresponding to general formula (I) where X$_1$ is acetyl (Ac), X$_2$ is Lys and X$_3$ is Phe.

Also preferred are peptides defined by the sequence SEQ_ID_NO: 1 to SEQ_ID_NO: 25, and which have the amino acid of the N-terminal end functionalized with the p-toluene sulphonyl group, and the amino acid of the C-terminal end in the form of carboxamide group.

Within this group particularly preferred are the peptides defined by the sequences SEQ_ID_NO: 1, 6, 11 and 16, and which have the amino acid of the N-terminal end functionalized with the p-toluene sulphonyl group, and the amino acid of the C-terminal end in the form of carboxamide group.

Even more preferred is the peptide defined by the sequence SEQ_ID_NO: 1, and which has the amino acid of the N-terminal end functionalized with the p-toluene sulphonyl group, and the amino acid of the C-terminal end in the form of carboxamide group. Said peptide has the structure Ts-Lys-Lys-Leu-Phe-Lys-Lys-Ile-Leu-Lys-Phe-Leu-NH$_2$, corresponding to general formula (I) where $X_1$ is p-toluene sulphonyl (Ts), $X_2$ is Lys and $X_3$ is Lys.

Also preferred are the peptides defined by the sequences of amino acids SEQ_ID_NO:1 to SEQ_ID_NO: 25, and which have the amino acid of the N-terminal end functionalized with the benzyl group, and the amino acid of the C-terminal end in the form of carboxamide group.

Within this group is especially preferred the peptide defined by SEQ_ID_NO: 15, and which has the amino acid of the N-terminal end functionalized with the benzyl group, and the amino acid of the C-terminal end in the form of carboxamide group. Said peptide has the structure Bn-Trp-Lys-Leu-Phe-Lys-Lys-Ile-Leu-Lys-Val-Leu-NH$_2$, corresponding to general formula (I) where $X_1$ is benzyl (Bn), $X_2$ is Trp and $X_3$ is Val.

Also preferred are the peptides defined by the sequences of amino acids SEQ_ID_NO:1 to SEQ_ID_NO: 25, and which have the amino acid of the N-terminal end functionalized with the benzoyl group, and the amino acid of the C-terminal end in the form of carboxamide group.

Within this group is especially preferred the peptide defined by SEQ_ID_NO: 1 and SEQ_ID_NO: 11, and which has the amino acid of the N-terminal end functionalized with the benzoyl group, and the amino acid of the C-terminal end in the form of carboxamide group. Said peptide has the structure Bz-Lys-Lys-Leu-Phe-Lys-Lys-Ile-Leu-Lys-Lys-Leu-NH$_2$, corresponding to general formula (I) where $X_1$ is benzoyl (Bz), $X_2$ is Lys and $X_3$ is Lys.

The peptides described in the invention are formed by 11 amino acids which make them appropriate to be prepared using the habitual procedures of solid-phase peptide synthesis, described by R. B. Merrifield. J. Am. Chem. Soc., 1963, 85. 2149-2154.

Among them we can mention that which uses as solid support 4-methyl-benzhydrylamine resin (MBHA) functionalized with amino groups. On said solid support are carried out the successive reactions of coupling between the different amino acids which integrate the peptide.

Said procedure is well known by the person skilled in the art and is described, for example, in S. A. Kates, F. Albericio Eds., Solid-Phase Synthesis. A practical guide, Marcel Dekker, New York, 2000 [ISBN:0-8247-0359-6], or in K. Burgess Eds., Solid-Phase Organic Synthesis, Wiley, John & Sons, New York, 1999 [ISBN: 0471318256].

When the MBHA resin is used as solid support, said resin is typically incorporated in a bifunctional spacer sensitive to the acid medium, which permits the deanchoring in mild conditions of the peptide once synthesized.

For example, an appropriate bifunctional spacer is Fmoc-Rink-Linker (CAS number: 145469-56-3) marketed by the company Senn Chemicals (Switzerland).

Said spacer, once it has bound through its carboxylic group to the amino group of the MBHA resin, and the protector group Fmoc has been eliminated, it has a free amino group which permits the anchoring of an amino acid which has a free carboxylic group.

In the market it is possible to acquire the Fmoc-Rink-MBHA resin in the company Senn Chemicals, which already has said spacer incorporated.

A procedure for the preparation of the peptides of the invention may be, for example, that described below.

Said procedure uses the chemical of the Fmoc group (9-fluoro-enyl-methoyl-oxy-carbonyl) as protector of the α-amino group of the amino acids that are used to prepare the peptides of the invention.

For the protection of the lateral chain of the lysine (Lys) and of tryptophan (Trp) the group tert-butyloxycarbonyl (Boc) has been used. For the protection of the lateral chain of the tyrosine (Tyr) the group tert-butyl (t-Bu) has been used.

In the first stage the protector group Fmoc, present in the amino group of the bifunctional spacer, is eliminated. Next, the anchoring of the amino acid leucine occurs, which as has the α-amino group protected by the Fmoc group.

Before proceeding with the new coupling, the Fmoc protector group is eliminated from the leucine anchored in the resin.

The coupling-deprotection cycle is repeated until completing the peptide structure.

The incorporation of the last two amino acids of the peptide are habitually carried out by 2 or 3 successive couplings in order to complete the coupling reaction of the amino acid with the peptide anchored in the resin.

The excision of the peptide from the solid support is carried out in acid conditions, at the same time as the protector groups are eliminated from the lateral chains of the amino acids which form the peptide.

After a conventional isolation process, the peptides of the invention are obtained with good purity, typically over 90%, determined by HPLC, in the form of powder solids, and they are characterized by mass spectrometry (ESI-MS).

Surprisingly, it has been verified that the peptides of the invention have an antimicrobial activity, which is particularly effective to combat pathogenic microorganisms of the plants such as the bacteria *Erwinia amylovora*, *Xanthomonas vesicatoria* and *Pseudomonas syringae*.

Part of the object of the invention is the use of the peptides of the invention to prepare an antimicrobial composition.

Preferably, the peptides of the invention are used as antimicrobial agents to combat pathogenic bacteria of the plants.

Preferably, the phytopathogenic bacteria are selected from the group formed by *Erwinia amylovora*, *Xanthomonas vesicatoria* and *Pseudomonas syringae*.

Among the peptides of the invention which are preferred to be used as antimicrobial agents to combat pathogenic bacteria of plants, are the preferred peptides mentioned previously in this same section.

Said bacteria are appropriate indicators to determine the antimicrobial activity of compounds which can be used to combat infections and diseases caused by bacteria in plants.

*Erwinia amylovora* is a Gram negative bacteria which causes the disease known as fire blight which affects the plants of the family of rosaceae, among which are the fruit trees of great economic importance such as apple trees and pear trees, ornamental plants such as sorb-tree, hawthorn and criping fruited service tree. In Europe it is classified as a quarantine bacteria in agriculture. Fire blight may affect practically all plant organs and frequently involves the death of the diseased trees or bushes. There are currently no effective methods to control fire blight and it is necessary to combine different measures aimed at eliminating or reducing the inoculum.

*Xanthomonas vesicatoria* is a Gram negative bacteria which causes the disease called bacterial fruit blotch in plants of the family of the Solanaceae which have a great economic importance such as tomato and pepper. This disease affects leaves, stems and fruit causing its wilting or death.

*Pseudomonas syringae* is a Gram negative bacteria which causes a large number of diseases called bacterial necrosis in plants of horticultural and woody cultures such as fruit trees. The pathogenicity of *P. syringae* lies in many cases in its ice nucleation activity (INA+) which boosts damages due to ice, and the production of various phytotoxins such as syringomycins.

Preferably, the plants which can be treated with the peptides of the invention are selected from the group formed by fruit trees, horticultural plants and ornamental plants.

Among the fruit trees we can mention those of pip (apple, pear) and stone (peach tree, apricot tree, plum tree, cherry tree) and the banana tree.

Among the horticultural plants we have Solanaceae (tomato, pepper, potato) and cucurbitaceae (melon, watermelon)

Among the horticultural plants are sorb-tree, carnation, hawthorn and criping fruited service tree.

Phytosanitary Compositions

A phytosanitary composition which comprises the following is also part of the object of the invention:

a linear peptide which response to general formula (I):

$$X_1\text{-}X_2\text{-Lys-Leu-Phe-Lys-Lys-Ile-Leu-Lys-}X_3\text{-Leu-}NH_2 \quad (I)$$

wherein $X_1$ is hydrogen, acetyl, p-toluene sulphonyl, benzyl or benzoyl, $X_2$ is Lys, Tyr, Leu, Phe, or Trp and $X_3$ is Lys, Tyr, Val, Phe or Trp, with the condition that the peptide wherein $X_1$ is hydrogen, $X_2$ is Trp and $X_3$ is Val is expressly excluded, and an auxiliary agent.

Among the peptides of the invention that are preferred to form part of said phytosanitary compositions are the peptides mentioned as preferred in the previous section called Peptides.

The phytosanitary compositions of the invention have good antimicrobial properties to combat pathogenic bacteria of plants.

Typically, in the antimicrobial compositions various active principles are combined to obtain a greater efficacy of a wider action spectrum. In this case, the phytosanitary compositions of the invention may also comprise other antimicrobial activity to achieve greater antimicrobial efficacy, such as, for example, the combination of several peptides of the invention, or their combination with other different active materials.

The peptides of the invention may also be combined with antifungal agents, and thus deploy a wider antimicrobial action.

The quantity of peptide which forms part of the phytosanitary composition may be variable in accordance with factors such as plant type, the concentration of pathogenic bacteria in the plant, the extension of disease, etc. The effective concentration of the peptide can be easily determined and adjusted using routine well-known methods known by the person skilled in the art. Typically, the effective concentration of the peptide is between 0.01 and 0.5 g/l.

The auxiliary agent which accompanies the peptides of the invention in said phytosanitary compositions may have several functions, such as, for example, facilitating the dosing of the peptide, providing a product which is easily handled, improving the wetting of the plants with the phytosanitary composition.

Said auxiliary agents can be selected from the group formed by: solvents, diluents, inert fillers, wetting surfactant agents, buffering agents, dispersant agents, anti-caking agents, lubricants, ultraviolet radiation filters and/or mixtures thereof.

Preferably, the auxiliary agent is selected from the group formed by solvents, surfactants, buffering agents, ultraviolet radiation filters and/or mixtures thereof.

Very preferably, the solvent is water.

The compositions can be presented in liquid form or in solid form. For example, in the case of liquid formulations, the composition of the invention may be in the form of a diluted composition ready to be used, or in the form of a concentrated agent, which requires its dilution before being used, typically with water.

In the case of the aqueous liquid compositions, the presence of wetting surfactant agents facilitates the wetting of the plants when they are sprayed with said composition.

An advantage of the peptides of the invention is that they can be dissolved in water easily, and they can be formulated generally as aqueous solutions without the need to use additional organic solvents.

The compositions in solid form can be in the form of granules or powders, wherein the peptides of the invention are mixed with inert fillers finely divided such as, for example, kaolin, diatomaceous earth, dolomite, calcium carbonate or talc. They can also be presented in the form of dispersible granules or powders, which comprise a wetting agent to facilitate the dispersion thereof in liquid.

Part of the object of the invention is also a method to prevent and treat plant and infections caused by bacteria which comprise placing in contact the plant with a phytosanitary composition which includes the peptides of the invention.

In the method of the invention, the phytosanitary composition can be applied in preventive form to the plants to avoid the appearance of infections and diseases caused by bacteria. The preventive treatment has its basis in the fact that the peptides of the invention inhibit the growth of pathogenic bacteria of the plants.

In the method of the invention, the phytosanitary composition can also be used to treat said infections and diseases once their presence has been detected in the plants, since the peptides of the invention inhibit the growth of the bacteria causing said infections and diseases.

In this description, the term infection relates to the invasion and destruction of an organ, for example, leaves, flowers or fruits, by the pathogenic microorganisms. Therefore, it is a localized process. Instead, the term disease relates to a process which affects the plant, giving rise to symptoms.

Preferably, the method of the invention is used to prevent and treat inventions and diseases caused by pathogenic bacteria of the plants selected from the group formed by *Erwinia amylovora, Xanthomonas vesicatoria* and *Pseudomonas syringae.*

Preferably, the plants which can be treated with the peptides of the invention are selected from the grouped formed by fruit trees, horticultural trees and ornamental plants.

In the method of the invention, the composition can be placed in contact with the parts of the plants selected among the group formed by seeds, roots, stems, leaves or fruit, or with the soil or any method of growth which surrounds the routes of the plants.

In the method of the invention, the phytosanitary composition can be placed in contact with the plant by any conventional technique, among which are highlighted spraying, immersion or watering.

For example, an aqueous solution can be prepared of the peptides of the invention and the parts of the plant affected or susceptible of being affected being sprayed. If they are fruit from a fruit tree, for example, their treatment can also be performed by the spraying or immersion before their harvesting or in the post-harvest.

The treatment of the roots can be carried out, for example, using a solid composition wherein the peptides are dispersed in an inert filler, or by spraying with said aqueous solution or by its application by watering.

Biological Tests

The antimicrobial activity of the peptides of the invention to combat pathogenic bacteria for plants has been evaluated by the determination of the concentration of the minimum peptide necessary to inhibit the growth of microorganisms. Typically, said concentration is called minimum inhibitory concentration (MIC).

This type of test is typical in microbiology and it is well known by the person skilled in the art. A description of the methodology used is found for example, in M. J. Pelczar, E. C. S. Chan, N. R. Krieg, Microbiology: Concepts and Applications. New York: McGraw-Hill, 1997.

To evaluate said antimicrobial effect of the peptides of the invention the following strains of pathogenic bacterial were used *Erwinia amylovora* PMV6076 (INRA, Angers, France) *Xanthomonas vesicatori* 2133-2 (IVIA, Valencia, Spain) and *Pseudomonas syringae* EPS94 (IN-TEA, Universitat de Girona, Spain).

It has been verified that the compositions which comprise the peptides of the invention dissolved in water at concentrations between 2.5 and 7.5 μM are effective to inhibit the growth of bacteria such as *Erwinia amylovora, Xanthomonas vesicatoria* and *Pseudomonas syringae*.

These results show the efficacy of the antimicrobial activity of the peptides of the invention, since in Avrahami et al, Biochemistry, 2001, 40, 12591-12603, a minimum inhibitory concentration less than 50 μm is considered significant.

The peptides of the invention are more effective to combat said bacteria than the peptide described by Cavallarin et al, defined by the sequence SEQ_ID_NO:15 and which has the C-terminal end in the form of carboxamide group, since this peptide has minimum inhibitory concentrations over 7.5 μM, when it is tested against *Erwinia amylovora, Xanthomonas vesicatoria* and *Pseudomonas syringae* bacteria.

The haemolytic activity of the peptides is an indicator of the toxicity of eukaryotic cells, and a characteristic which is generally determined for those compounds which may come into contact with the human body. This would be the case if fruit or vegetables treated with the peptides of the invention contained residues thereof and they were consumed by people, or handled by operators during their application or preparation.

Said haemolytic activity has been evaluated by the determination of the release of haemoglobin which is produced on placing a solution of said peptides in contact with the TRIS buffer with 5% volume/volume erythrocyte suspension from fresh human blood. The result of said determination is expressed as the percentage of haemolysis which is produced for a known concentration of peptide. A description of the methodology used to determine the haemolytic activity is found in Oren et al, Biochemistry, 2000, 39, 6103-6114, and in Raguse et al., J. Am. Chem. Soc., 2002, 124, 12774-12785.

It has been verified that the large majority of the peptides of the invention have a significant haemolytic activity at a concentration which is between ten and one hundred times greater than the concentration at which they are active to inhibit the growth of the pathogenic bacteria of plants.

The stability of the peptides to degradation by proteases is a characteristic which permits evaluating that the peptides are unaltered in the environment of the plant during a reasonable half life time. The peptides can be degraded both by protease present in the tissue of the plants and in the ephyticic microorganisms.

The stability of the peptides to degradation by proteases has been evaluated by the treatment of peptide solutions in TRIS buffer with Proteinase K (Sigma-Aldrich), and the monitoring of their degradation by HPLC at different time intervals. The degradation is expressed as the percentage of peptide degraded after a determined time interval calculated from the decrease in the area of the peak of the native peptide by HPLC. A description of the methodology used by the determination of the stability to proteases is found in Rozek et al, Biochemistry, 2003, 42, 14130-14138.

It has been verified that some peptides of the invention are more stable to degradation by proteases than the peptide described by Cavallarin et al. Next, for the purpose of sufficiently completing the previous description, the following examples are given.

EXAMPLES

In the following examples, the following abbreviations are used: Ac: acetyl; Ac$_2$O: acetic anhydride; Bn: benzyl; Boc: tert-butyloxycarbonyl; t-Bu: tert-butyl; Bz: benzoyl; MIC: minimum inhibitory concentration; DIAE: N,N-diisopropylethylamine; DMF: N,N-dimethylformamide; EDTA, ethylenediaminetetraacetic acid; ESI-MS: electrospray ionization tandem mass spectrometry; Fmoc: 9-fluoro-enyl-methoyloxy-carbonyl; HBTU: N-[1H-benzotriazol(1-yl)(dimethylamino)methylene]-N-methylmethanaminium hexa-fluoro-phosphate-N-oxide; HPLC: high performance liquid chromatography; LB: Luria Bertani; MBHA: 4-methyl-benzhydrylamine; NMP: N-methyl-pyrrolidone; TFA: trifluoroacetic acid; TIS: triisopropylsilane; TRIS: tris(hydroxyl methane)amino methane; TS: p-toluene sulphonyl; TSB Trypticase Soy Broth: UV: ultraviolet.

The products Fmoc-Lys(Boc)-OH, Fmoc-Phe-OH, Fmoc-Leu-OH, Fmoc-Ile-OH, Fmoc-Tyr(tBu)-OH, Fmoc-Trp (Boc)-OH, Fmoc-Val-OH, the Fmoc-Rink-MBHA resin functionalized with amino groups, and HBTU, were obtained from Senn Chemicals. The products benzyl chloride, benzoyl chloride, trifluoroacetic acid, N-methyl-pyrrolidone and TIS were obtained from Aldrich. The products tosyl chloride, piperidine and DIAE were obtained from Fluka.

The following indications on the procedure for the preparation of the peptides are of general character:

Amino acids were used which have the α-amino groups protected with the Fmoc group.

For the protection of the lateral chain of the lysine and the tryptophan the group tert-butyloxycarbonyl (Boc) was used. For the protection of the lateral chain of the tyrosine, the group tert-butyl (t-bu) group was used.

The reactions were carried out in syringes of 2 or 5 ml which had incorporated a microporous filter.

All the transformations and washes were carried out at 25° C., unless indicated otherwise.

The HPLC analysis was carried out with a flow of 1.0 ml/min using a Kromasil reverse phase column (4.6×40 mm; particle size 3.5 µm). Linear gradients were used with 0.1% aqueous TFA in 0.1% acetronitrile, with a ratio between 0.98:0.02 and 0.98:0.1 during a period of time of 7 minutes with UV detection at a wavelength of 220 nm.

The ESI-MS spectrum were acquired using a four-pole Navigator instrument; operating in the positive ion mode (ES+) with a sample voltage of 30 kV.

All the ratios between the solvents are volume/volume, unless another type of proportion is specified.

Example 1

Preparation of H-Lys-Lys-Leu-Phe-Lys-Lys-Ile-Leu-Lys-Val-Leu-NH$_2$ (general formula (I) where $X_1$ is Hydrogen, $X_2$ is Lys and $X_3$ is Val)

In a 2 ml capacity syringe, equipped with a microporous filter in its lower part, 30 mg of Fmoc-Rink-MBHA resin were placed with a functionalization of 0.66 mmol/g, equivalent to 19.8 µmoles of amino groups, and the syringe was filled with solvent to swell-wash the resin in accordance with the following sequence: CH$_2$Cl$_2$ (1×20 min) and DMF (1×20 min). The expression CH$_2$Cl$_2$ (1×20 min) relates to the fact that 1 wash was carried out of 20 minutes with methylene chloride. After each washing stage, the solvent was eliminated by a multiple vacuum filter (Vac Man Laboratory Vacuum Manifold from Promega Distribuidora).

After swelling-washing the resin, this was treated with a mixture of piperidine and DMF (3:7, 1×2 min and 1×10 min) to eliminate the Fmoc group present in the amino group of the bifunctional spacer and, then, it was washed with DMF (6×1 min).

Next, the resin was treated with 21 mg of Fmoc-Leu-OH (59 µmoles), 22 mg of HBTU (59 µmoles) and 11 µl of DIAE (63 µmoles) in 0.1 ml of DMF. After 4 hours, the resin was washed with DMF (6×1 min) and it was checked that the ninhydrin test was negative (Kaiser et al, Anal. Biochem., 1970, 34, 595-598).

The elimination of the Fmoc group and the subsequent washes were carried out as described above.

The coupling-deprotection cycle was repeated for the following four amino acids protected with the group N$^\alpha$-Fmoc: Fmoc-Val-OH, Fmoc-Lys (Boc)-OH, Fmoc-Leu-OH and Fmoc-Ile-OH. In each stage it was washed with DMF (6×1 min).

After the fifth amino acid incorporated, the elimination of the Fmoc group, the coupling-deprotection cycles and the corresponding washes were performed in the same way substituting in these cases the DMF by NMP. The last six amino acids were incorporated protected with the N$^\alpha$-Fmoc group: Fmoc-Lys (Boc)-OH, Fmoc-Phe-OH and Fmoc-Leu-OH. For the incorporation of the last two amino acids, 2-3 successive couplings were performed to obtain a negative ninhydrin test.

After eliminating the Fmoc group of the last amino acid coupled, as has already been described, the resin was washed with NMP (6×1 min) and CH$_2$Cl$_2$ (6×1 min), and the linear peptide was obtained bound to the resin H-Lys-Lys-Leu-Phe-Lys-Lys-Ile-Leu-Lys-Val-Leu-Rink-MBHA. Next, the peptide was splitted from the resin by a treatment with 1 ml of a mixture of TFA, water and TIS (95:2, 5:2.5) during 2 hours. The filtrate was collected in a vial by a positive nitrogen pressure. The resin was washed with a mixture of TFA, water and TIS 95:2, 5:2.5, 2×0.5 ml). The filtrate was combined and was evaporated almost to dryness under a nitrogen current until obtaining an oil. Said oil was precipitated with diethyl ether, it was centrifuged and the ether was decanted. This process was repeated 3 or 4 times. Finally, the solid product obtained was dissolved in water and was lyophilized.

A powdery solid was obtained which had a purity over 90% analysed by HPLC (retention time 4.39 minutes) and its structure was confirmed by ESI-MS.

The synthesis of this peptide was also carried out on a greater scale using 200 mg of Fmoc-Rink-MBHA resin with a functionalization of 0.66 mmol/g, equivalent to 132 µmoles of amino groups, using a procedure described in this same Example 1.

Example 2

Preparation of Ac-Lys-Lys-Leu-Phe-Lys-Lys-Ile-Leu-Lys-Val-Leu-NH$_2$ (General Formula (I) where $X_1$ is Acetyl (Ac) $X_2$ is Lys and $X_3$ is Val)

The peptidylresin H-Lys-Lys-Leu-Phe-Lys-Lys-Ile-Leu-Lys-Val-Leu-Rink-MBHA obtained in Example 1 was treated with 0.2 ml of a mixture of acetic anhydride (Ac$_2$O), pyridine and CH$_2$Cl$_2$ (1:1:1) during 1 h at ambient temperature. Then, the resin was washed with CH$_2$Cl$_2$ (6×1 min).

Next. The peptide was splitted from the resin and was isolated by following the procedure described in Example 1. The purity of the peptide obtained was over 90% determined by HPLC (retention time 4.59 minutes), and its structure was confirmed by EMI-MS.

Example 3

Preparation of Ts-Lys-Lys-Leu-Phe-Lys-Lys-Ile-Leu-Lys-Val-Leu-NH$_2$ (General Formula (I) where $X_1$ is p-toluene sulphonyl (Ts) $X_2$ is Lys and $X_3$ is Val)

The peptidylresin H-Lys-Lys-Leu-Phe-Lys-Lys-Ile-Leu-Lys-Val-Leu-Rink-MBHA obtained in Example 1 was treated with p-toluene sulphonyl chloride (TsCl) (792 µmoles) and DIAE (1.58 mmoles) in 0.2 ml of a mixture of CH$_2$Cl$_2$ and NMP (9:1) during 1 h at ambient temperature. Then, the resin was washed with NMP (6×1 min).

Next. The peptide was splitted from the resin and was isolated by following the procedure described in Example 1. The purity of the peptide obtained was over 90% determined by HPLC (retention time 4.59 minutes), and its structure was confirmed by EMI-MS.

Example 4

Preparation of Bz-Lys-Lys-Leu-Phe-Lys-Lys-Ile-Leu-Lys-Val-Leu-NH$_2$ (General Formula (I) where $X_1$ is benzoyl (Bz) $X_2$ is Lys and $X_3$ is Val)

The peptidylresin H-Lys-Lys-Leu-Phe-Lys-Lys-Ile-Leu-Lys-Val-Leu-Rink-MBHA obtained in Example 1 was treated with benzoyl chloride (BzCl) (792 µmoles) and DIAE (1.58 mmoles) in 0.2 ml of a mixture of CH$_2$Cl$_2$ and NMP (9:1) during 1 h at ambient temperature. Then, the resin was washed with NMP (6×1 min).

Next. The peptide was splitted from the resin and was isolated by following the procedure described in Example 1. The purity of the peptide obtained was over 90% determined by HPLC (retention time 5.00 minutes), and its structure was confirmed by EMI-MS.

Example 5

Preparation of Bn-Lys-Lys-Leu-Phe-Lys-Lys-Ile-Leu-Lys-Val-Leu-NH$_2$ (General Formula (I) where X$_1$ is benzyl (Bn) X$_2$ is Lys and X$_3$ is Val)

The peptidylresin H-Lys-Lys-Leu-Phe-Lys-Lys-Ile-Leu-Lys-Val-Leu-Rink-MBHA obtained in Example 1 was treated with benzyl bromide (BnBr) (792 µmoles) and DIAE (1.58 mmoles) in 0.2 ml of a mixture of CH$_2$Cl$_2$ and NMP (9:1) during 48 h at ambient temperature. Then, the resin was washed with NMP (6×1 min).

Next. The peptide was splitted from the resin and was isolated by following the procedure described in Example 1. The purity of the peptide obtained was over 90% determined by HPLC (retention time 4.73 minutes), and its structure was confirmed by EMI-MS

Example 6

Preparation of a Chemical Library of Linear Peptides in Solid Phase

A chemical library was designed to obtain 125 peptides, which respond to general formula (I):

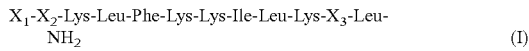

X$_1$-X$_2$-Lys-Leu-Phe-Lys-Lys-Ile-Leu-Lys-X$_3$-Leu-NH$_2$   (I)

Wherein

X$_1$ is hydrogen, acetyl, p-toluene sulphonyl, benzyl or benzoyl,

X$_2$ is Lys, Tyr, Leu, Phe, or Trp and

X$_3$ is Lys, Tyr, Val, Phe or Trp, with the condition that the peptide wherein X$_1$ is hydrogen, X$_2$ is Trp and X$_3$ is Val is expressly excluded, from the peptides of the invention.

In five syringes of 5 ml capacity, correctly labelled and equipped with a microporous filter in the lower part, were placed 350 mg of Fmoc-Rink-MBHA resin with a functionalization of 0.66 mmol/g, equivalent to 231 µmoles of the amino groups. The syringes were filled with a solvent to swell-wash the resin in accordance with the following sequence: CH$_2$Cl$_2$ (1×20 min) and DMF (1×20 min). After each stage of washing, the solvent was eliminated by a multiple vacuum filter (Vac Man Laboratory Vacuum Manifold by Promega Distribuidora).

After swelling-washing the resins they were treated with a mixture of piperidine and DMF (3:7, 1×2 min and 1×10 min) to eliminate the Fmoc group present in the amino group of the bifunctional spacer and, then, they were washed with DMF (6×1 min).

Then, the five resins were treated with 245 mg of Fmoc-Leu-OH (693 µmoles), 263 mg of HBTU (693 µmoles) and 121 µl of DIAE µl (693 µmoles) in 0.8 ml of DMF. After 4 hours, the resins were washed with DMF (6×1 min) and it was verified that the ninhydrin test was negative (Kaiser, Anal. Biochem., 1970, 34, 595-598).

Next, the Fmoc group was eliminated and the corresponding washes were carried out as previously described. Then, the corresponding amino acid X$_3$ was coupled to each resin: Fmoc-Val-OH, Fmoc-Trp(Boc)-OH, Fmoc-Tyr(Boc)-OH, Fmoc-Phe-OH or Fmoc-Lys(Boc)-OH, following the procedure used to couple the protected amino acid Fmoc-Leu-OH.

The elimination of the Fmoc group and the subsequent washes were performed as described above.

The coupling-deprotection cycle was repeated for the following three amino acids. In this way, the following were sequentially coupled: Fmoc-Lys(Boc)-OH, Fmoc-Leu-OH and Fmoc-Ile-OH. These couplings were performed of each one of the five resins. In each stag the washing was performed with DMF (6×1 min).

After the fifth amino acid incorporated the elimination of the Fmoc group, the coupling-deprotection cycles and the corresponding washes were performed in the same way substituting in these cases the use of DMF for that of NMP. Following this procedure, to each one of the five resins were sequentially coupled two residues of Fmoc-Lys(Boc)-OH, one of Fmoc-Phe-OH and one of Fmoc-Leu-OH. In each stage, it was washed with NMP (6×1 min). For the incorporation of the tenth residue it was necessary to have a double coupling to obtain a negative ninhydrin test.

Once the tenth residue was coupled, each one of the peptidylresins confined in the five syringes, it was divided in five fractions. The 25 fractions obtained, corresponding to approximately 46 µmoles of peptidylresin each, were placed in 25 syringes of 2 ml capacity, suitably labelled and equipped with a microporous filter in the lower part. Then, the Fmoc was eliminated and the corresponding washes were carried out as previously described. To each one of the five fractions of resins which have the same X$_3$ amino acid incorporated the corresponding X$_2$ residue was coupled: Fmoc-Trp(Boc)-OH, Fmoc-Phe-OH, Fmoc-Tyr(tBu)-OH, Fmoc-Lys(Boc) or Fmoc-Leu-OH. The couplings were carried out using 138 µmoles of the amino acid N$^\alpha$-Fmoc protected corresponding, 138 µmoles of DIAE in 0.3 ml of NMP. To incorporate these amino acids, it was necessary to performing a double coupling to obtain a negative ninhydrin test.

Next, each of the 125 previous fractions was divided in five equal fractions. The 125 fractions of resin obtained, corresponding to approximately 9.2 µmoles of peptidylresin, were placed in 125 syringes of 2 ml capacity, suitably labelled and equipped with a microporous filter in its lower part. Next, the Fmoc group was eliminated and the corresponding washes were carried out as previously described.

Four of the five fractions of resin obtained from each of the 25 previous fractions were derived at the N-terminal end by acetylation, tosylation, benzoylation or benzylation, respectively, The acetylation was carried out by treatment with 0.2 ml of a mixture of Ac$_2$O, pyridine and CH$_2$Cl$_2$ (1:1:1) during 1 h at ambient temperature.

The tosylation was carried out by treatment with TsCl (368 µmoles) and DIAE (736 µmoles) in 0.2 ml of a mixture of CH$_2$Cl$_2$ and NMP (9:1) during 1 h at ambient temperature.

The benzoylation was carried out by treatment with BzCl (368 µmoles) and DIAE (736 µmoles) in 0.2 ml of a mixture of CH$_2$Cl$_2$ and NMP (9:1) during 1 h at ambient temperature.

The benzylation was carried out by treatment with BnCl (368 µmoles) and DIAE (736 µmoles) in 0.2 ml of a mixture of CH$_2$Cl$_2$ and NMP (9:1) during 48 h at ambient temperature.

After these treatments, the resins were washed with NMP (6×1 min).

Finally, the excision of the 125 peptides of the resin occurred in the corresponding syringe and the isolation of each of them following the procedure described in Example 1.

The peptides obtained were analysed by HPLC and their structure was confirmed by ESI-MS. A purity over 90% was obtained in all cases.

Example 7

Microbial Activity Tests

The antimicrobial effect of the peptides of the invention was determined against the following bacterial strains

*Erwinia amylovora* PMV6076 (INRA, Angers, France) *Xanthomonas vesicatori* 2133-2 (IVIA, Valencia, Spain) and *Pseudomonas syringae* EPS94 (IN-TEA, Universitat de Girona, Spain).

All the bacteria were stored at a temperature of −80° C. in Luria-Bertani (LB) medium supplemented with 20% glycerine in volume/volume.

The suspensions of *Erwinia amylovora* PMV6076 and *P. syringae* EPS94 were obtained after a growth of 24 hours at 25° C. and, the sample of *X. vesicatori* 2133-2 was obtained after incubation during 48 hours at 25° C. in LB agar. In all cases they were resuspended in sterile water to obtain a suspension adjusted to an absorbance of 0.2 to 60 nm, which approximately corresponds to $10^8$ colony forming units.

To determine the minimum inhibitory concentration (MIC), the peptides were solubilized in milli-Q sterile water until a final concentration of 1000 μM and they were filtered through a 0.22 μm pore size filter.

Dilutions of the peptides of the invention were made to obtained solutions at the concentrations of 750, 500, 250, 200, 150, 125, 100, 75, 50 and 25 μM.

20 μl of each dilution were mixed with 20 μl of the suspension of the corresponding bacterial indicator, and 160 μl of the TSB (Trypticase Soy Broth) liquid medium until a total volume of 200 μl in each well of a microplate. Thus, the effective concentration at which the bacteria suspensions were subjected were 75, 50, 25, 20, 15, 12.5, 10, 7.5, 5 and 2.5 μM.

Two replicas were carried out for each strain, concentration and peptide under study.

The positive controls contained water instead of peptide, and the negative controls contained the peptides without the bacterial suspension.

The microbial growth was determined automatically by optical density at 600 nm using the Microbiology Analyser Bioscreen C (Labsystems)

The microplates were incubated at 25° C. for 48 hours with stirring for 20 seconds before measuring the absorbance every hour. Each experiment was performed twice.

As MIC, the lowest peptide concentration at which bacterial growth occurred at the end of the experiment was taken.

Table II shows the range of concentrations including the MIC, expressed in μM, after 48 h incubation at 25° C., for different peptides of the invention to combat the as *Erwinia amylovora, Xanthomonas vesicatoria* and *Pseudomonas syringae*. The peptides of Table II are identified with the parameters $X_1$, $X_2$ and $X_3$ which appear in general formula (I). Furthermore, Table II includes the reference number with relation to the chemical library prepared in Example 6. Table II includes as comparative example the results corresponding to the peptide described by Cavallarin et al, which does not form part of the invention.

TABLE II

| Ref. | $X_1$ | $X_2$ | $X_3$ | *P. syringae* | *X. vesicatoria* | *E. amylovora* |
|---|---|---|---|---|---|---|
| Comparative example | H | Trp | Val | >7.5 | >7.5 | >7.5 |
| BP017 | H | Lys | Trp | 5-7.5 | 5-7.5 | >7.5 |
| BP100 | H | Lys | Tyr | 2.5-5 | 5-7.5 | 2.5-5 |
| BP095 | H | Tyr | Tyr | 5-7.5 | 2.5-5 | 5-7.5 |
| BP105 | H | Leu | Tyr | 5-7.5 | 2.5-5 | 5 |
| BP090 | H | Phe | Tyr | 5-7.5 | 2.5-5 | 5-7.5 |
| BP020 | H | Trp | Tyr | 2.5-5 | 2.5-5 | 2.5-5 |
| BP015 | H | Lys | Val | 2.5-5 | >7.5 | 5-7.5 |
| BP033 | H | Leu | Val | 5-7.5 | >7.5 | 5-7.5 |
| BP076 | H | Lys | Phe | 2.5-5 | 2.5-5 | 2.5-5 |
| BP081 | H | Leu | Phe | 2.5-5 | <2.5 | 2.5-5 |

TABLE II-continued

| Ref. | $X_1$ | $X_2$ | $X_3$ | *P. syringae* | *X. vesicatoria* | *E. amylovora* |
|---|---|---|---|---|---|---|
| BP066 | H | Phe | Phe | 5-7.5 | 2.5-5 | 2.5-5 |
| BP019 | H | Trp | Phe | 5-7.5 | 2.5-5 | 5-7.5 |
| BP052 | H | Lys | Trp | 5 | 2.5-5 | 2.5-5 |
| BP047 | H | Tyr | Trp | 5-7.5 | 2.5-5 | 5-7.5 |
| BP018 | H | Trp | Trp | 5-7.5 | 2.5 | 5-7.5 |
| BP120 | Ac | Tyr | Lys | 5-7.5 | 5-7.5 | >7.5 |
| BP101 | Ac | Lys | Tyr | 5-7.5 | 2.5 | >7.5 |
| BP029 | Ac | Lys | Val | 5-7.5 | 7.5 | 5-7.5 |
| BP077 | Ac | Lys | Phe | 5-7.5 | <2.5 | 5-7.5 |
| BP053 | Ac | Lys | Trp | 5-7.5 | 2.5-5 | >7.5 |
| BP038 | Ac | Trp | Trp | >7.5 | <2.5 | >7.5 |
| BP125 | Ts | Lys | Lys | 2.5-5 | 2.5-5 | >7.5 |
| BP121 | Ts | Tyr | Lys | 2.5-5 | 2.5-5 | >7.5 |
| BP102 | Ts | Lys | Tyr | 2.5-5 | <2.5 | 5-7.5 |
| BP097 | Ts | Tyr | Tyr | >7.5 | <2.5 | >7.5 |
| BP030 | Ts | Lys | Val | 5-7.5 | 5-7.5 | 5-7.5 |
| BP078 | Ts | Lys | Phe | 5-7.5 | <2.5 | 5-7.5 |
| BP054 | Ts | Lys | Trp | 5-7.5 | <2.5 | >7.5 |
| BP059 | Ts | Leu | Trp | >7.5 | 2.5 | >7.5 |
| BP011 | Bn | Trp | Val | 5-7.5 | 2.5-5 | 5-7.5 |
| BP126 | Bz | Lys | Lys | 2.5-5 | 2.5-5 | 5-7.5 |
| BP122 | Bz | Tyr | Lys | 5-7.5 | 2.5-5 | >7.5 |
| BP103 | Bz | Lys | Tyr | 5-7.5 | <2.5 | 7.5 |
| BP031 | Bz | Lys | Val | 5-7.5 | <2.5 | 2.5-5 |
| BP010 | Bz | Trp | Val | >7.5 | <2.5 | >7.5 |
| BP055 | Bz | Lys | Trp | >7.5 | <2.5 | >7.5 |

It is possible to verify that the peptides of the invention have a good efficacy to inhibit the growth of *Erwinia amylovora, Xanthomonas vesicatoria* and/or *Pseudomonas syringae.*

Furthermore, the efficacy of the peptides of the invention is greater than that of the already known peptide, whose results were presented in the first row of the previous table under the name of Comparative example.

Example 8

Haemolytic Activity Tests

The haemolytic activity of the peptides of the invention was evaluated by determining the release of haemoglobin which is produced on placing in contact a solution of the peptides with a suspension of erythrocytes 5% by volume, from fresh human blood.

The blood was collected aseptically using a Vactainer® K2E system (Belliver, Great Britain) with EDTA and it was stored at 4° C. for a period lower than 2 hours.

The blood was centrifuged at 6000 g for 5 minutes to separate the erythrocytes. There were washed three times with TRIS buffer (10 mM TRIS, 150 mM NaCl, pH 7.2) and they were resuspended in TRIS buffer until obtaining a suspension which contained 10% by volume of erythrocytes.

The peptides were solubilized in TRIS buffer until a final concentration of 100, 300 and 500 μM The replicas were used for each peptide and concentration. 65 μl of 10% erythrocyte suspension was mixed with 65 μl of the peptide solution in each well of a 96-well plate (MicroAmp®, Applied Biosystems, USA) (5% by volume of erythrocytes) and the mixture was incubated for 1 h at 37° C. under stirring. In this way, the erythrocyte suspensions were subjected to peptide concentrations of 50, 150 and 250 μM.

Next, the plates were centrifuged at 3500 g during 10 minutes and aliquots were transferred of 80 μl of supernatant to microplates with 100 wells (Bioscreen), which were diluted with 80 μl of milli-Q water.

The degree of haemolysis was determined from the absorbance at 540 nm with a Bioscreen plate reader.

The complete positive haemolysis control was determined in a TRIS buffer solution which contained 200 μM melittin (Sigma-Aldrich, Spain)

The percentage of haemolysis (H) was determined using the following equation:

$$H = 100 \times [(Op-Ob)/(Om-Ob)]$$

Where OP as the optical density measured for a determined peptide concentration, Ob was the optical density of the buffer solution, and Om was the optical density for the positive control with melittin.

Table III shows the results of haemolytic activity, expressed as percentage of haemolysis calculated according to the previous equation, for concentrations of peptides of the invention corresponding to 50, 150 and 250 μM. The peptides of Table III were identified with the parameters $X_1$, $X_2$ and $X_3$ which appear in general formula (I). Furthermore, Table III includes the reference number with relation to the chemical library prepared in Example 6:

TABLE III

| Ref. | $X_1$ | $X_2$ | $X_3$ | % Haemolysis 50 μM | % Haemolysis 150 μM | % Haemolysis 250 μM |
|---|---|---|---|---|---|---|
| BP119 | H | Tyr | Lys | 4 | 19 | 45 |
| BP100 | H | Lys | Tyr | 3 | 22 | 43 |
| BP095 | H | Tyr | Tyr | 7 | 50 | 76 |
| BP105 | H | Leu | Tyr | 14 | 91 | 90 |
| BP090 | H | Phe | Tyr | 11 | 57 | 84 |
| BP020 | H | Trp | Tyr | 78 | 77 | 72 |
| BP015 | H | Lys | Val | 0 | 16 | 45 |
| BP033 | H | Leu | Val | 4 | 38 | 68 |
| BP076 | H | Lys | Phe | 3 | 34 | 65 |
| BP081 | H | Leu | Phe | 10 | 65 | 88 |
| BP066 | H | Phe | Phe | 9 | 63 | 89 |
| BP019 | H | Trp | Phe | 57 | 94 | 100 |
| BP128 | H | Leu | Lys | 2 | 31 | 66 |
| BP052 | H | Lys | Trp | 51 | 84 | 79 |
| BP047 | H | Tyr | Trp | 81 | 76 | 82 |
| BP018 | H | Trp | Trp | 78 | 68 | 74 |
| BP124 | Ac | Lys | Lys | 1 | 5 | 23 |
| BP101 | Ac | Lys | Tyr | 4 | 31 | 62 |
| BP096 | Ac | Tyr | Tyr | 47 | 86 | 85 |
| BP077 | Ac | Lys | Phe | 6 | 40 | 81 |
| BP053 | Ac | Lys | Trp | 60 | 82 | 85 |
| BP038 | Ac | Trp | Trp | 80 | 86 | 80 |
| BP125 | Ts | Lys | Lys | 2 | 8 | 23 |
| BP121 | Ts | Tyr | Lys | 22 | 81 | 86 |
| BP102 | Ts | Lys | Tyr | 39 | 79 | 80 |
| BP097 | Ts | Tyr | Tyr | 83 | 81 | 88 |
| BP030 | Ts | Lys | Val | 25 | 70 | 80 |
| BP078 | Ts | Lys | Phe | 40 | 85 | 95 |
| BP126 | Bz | Lys | Lys | 2 | 14 | 24 |
| BP122 | Bz | Tyr | Lys | 32 | 78 | 96 |
| BP103 | Bz | Lys | Tyr | 42 | 83 | 80 |
| BP031 | Bz | Lys | Val | 34 | 71 | 76 |
| BP010 | Bz | Trp | Val | 77 | 77 | 76 |
| BP011 | Bn | Trp | Val | 81 | 96 | 100 |

In all cases it is observed that the concentration at which a significant haemolysis would occur is between 10 and 100 times greater than the concentration at which the peptides of the invention have antimicrobial activity.

Example 9

Tests of Stability to Protease Degradation

The stability of the peptides of the invention to degradation by proteases is determined by a peptide digestion test by Proteinase K (Sigma-Aldrich Corporation, Madrid, Spain).

A solution of 50 μg/ml of the peptide and 1 μg/ml of Proteinase K in 100 mM TRIS buffer at pH 7.6 was used, at ambient temperature.

The progress of the peptide excision was determined chromatographically at times between 5 and 45 minutes. To do this a reverse phase $C_{18}$ column was used (Kromasil, 4.6×40 mm; 3.5 μm particle size), and linear gradients from 0.98:0.02 to 0:1 during 7 min performing the detection by absorbance in ultraviolet light at 220 nm.

Table IV presents the results of stability to degradation by proteases, expressed as a percentage of degradation of each peptide after 45 minutes. The peptides of Table IV are identified with the parameters $X_1$, $X_2$ and $X_3$ which appear in general formula (I). Furthermore, Table IV includes the reference number with relation to the chemical library prepared in Example 6. Table IV includes as Comparative example the results corresponding to the peptide described by Cavallarin et al., which does not form part of the invention:

TABLE IV

| Ref. | $X_1$ | $X_2$ | $X_3$ | % Degradation in 45 minutes |
|---|---|---|---|---|
| Comparative example | H | Trp | Val | 100 |
| BP008 | Ac | Trp | Val | 100 |
| BP077 | Ac | Lys | Phe | 84 |
| BP009 | Ts | Trp | Val | 100 |
| BP125 | Ts | Lys | Lys | 67 |
| BP010 | Bz | Trp | Val | 100 |
| BP126 | Bz | Lys | Lys | 53 |
| BP015 | H | Lys | Val | 100 |
| BP019 | H | Trp | Phe | 87 |
| BP020 | H | Trp | Tyr | 85 |
| BP033 | H | Leu | Val | 100 |
| BP076 | H | Lys | Phe | 49 |
| BP100 | H | Lys | Tyr | 60 |

It can be observed that some peptides of the invention are more stable to degradation by proteases than the peptide described by Cavallarin et al. (Comparative example). In particular, the peptides corresponding to general formula (I) where $X_1$ is hydrogen, $X_2$ is Lys and $X_3$ is Phe, or $X_1$ is benzoyl, $X_2$ is Lys and $X_3$ is Lys, are two times more stable than the peptide of the Comparative example.

The invention claimed is:

1. A linear peptide selected from the general formula (I):

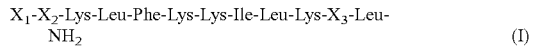   (I)

wherein
X₁ is hydrogen, acetyl, p-toluene sulphonyl, benzyl or benzoyl,
X₂ is Lys, Tyr, Leu, Phe, or Trp and
X₃ is Lys, Tyr, Val, Phe or Trp,
with the condition that the peptide wherein X1 is hydrogen or acetyl, X2 is Trp and X3 is Val is expressly excluded.

2. A peptide according to claim 1, selected from the sequences of SEQ ID NO: 1 to SEQ ID NO: 14, or SEQ ID NO: 16 to SEQ ID NO: 25, and wherein the C-terminal end of the sequence is a carboxamide group.

3. A peptide according to claim 2, selected from the sequences of SEQ ID NO: 6 to SEQ ID NO: 11, SEQ ID NO: 13, SEQ ID NO: 16, SEQ ID NO: 18 to SEQ ID NO: 22 or SEQ ID NO: 25, and wherein the C-terminal end of the sequence is a carboxamide group.

4. A peptide according to claim 3, selected from the sequences of SEQ ID NO: 6 and or SEQ ID NO: 16, and wherein the C-terminal end of the sequence is a carboxamide group.

5. A peptide according to claim 1, selected from the sequences of SEQ ID NO: 1 to SEQ ID NO: 14, or SEQ ID NO: 16 to SEQ ID NO: 25, and wherein the N-terminal end of the sequence is an acetyl group, and the C-terminal end of the sequence is a carboxamide group.

6. A peptide according to claim 5, wherein the sequence is SEQ ID NO: 25, and wherein the N-terminal end of the sequence is an acetyl group, and the C-terminal end of the sequence is a carboxamide group.

7. A peptide according to claim 1, selected from the sequences of SEQ ID NO: 1 to SEQ ID NO: 25, and wherein the N-terminal end of the sequence is a p-toluene sulphonyl group, and the C-terminal end of the sequence is a carboxamide group.

8. A peptide according to claim 7, selected from the sequences of SEQ ID NO: 1, SEQ ID NO: 6, SEQ ID NO: 11 and SEQ ID NO: 16, and wherein the N-terminal end of the sequence is a p-toluene sulphonyl group, and the C-terminal end of the sequence is a carboxamide group.

9. A peptide according to claim 8, wherein the sequence is SEQ ID NO: 1, and wherein the N-terminal end of the sequence is a p-toluene sulphonyl group, and the C-terminal end of the sequence is a carboxamide group.

10. A peptide according to claim 1, selected from the sequences of SEQ ID NO: 1 to SEQ ID NO: 25, and wherein the N-terminal end of the sequence is a benzyl group, and the C-terminal end of the sequence is a carboxamide group.

11. A peptide according to claim 10, wherein the sequence is SEQ ID NO: 15, and wherein the N-terminal end of the sequence is a benzyl group, and the C-terminal end of the sequence is a carboxamide group.

12. A peptide according to claim 1, selected from the sequences of SEQ ID NO: 1 to SEQ ID NO: 25, and wherein the N-terminal end of the sequence is a benzoyl group, and the C-terminal end of the sequence is a carboxamide group.

13. A peptide according to claim 12, selected from the sequences of SEQ ID NO: 1 and or SEQ ID NO: 11, and wherein the N-terminal end of the sequence is a benzoyl group, and the C-terminal end of the sequence is a carboxamide group.

14. A peptide according to claim 13, wherein the sequence is SEQ ID NO: 1, and wherein the N-terminal end of the sequence a benzoyl group, and the C-terminal end of the sequence is a carboxamide group.

15. A phytosanitary composition comprising a peptide according to claim 1, and an auxiliary agent.

16. The composition according to claim 15, wherein the peptide is found at a concentration between 0.01 and 0.5 g/l.

17. The composition according to claim 15, wherein the auxiliary agent is selected from the group consisting of solvents, surfactants, buffering agents, ultraviolet radiation filters and/or mixtures thereof.

18. The composition according to claim 17, wherein the solvent is water.

19. A method to prevent and treat plant infections and disease caused by bacterial which comprises contacting the plant with a phytosanitary composition according to claim 15.

20. A method according to claim 19, wherein the bacteria are selected from the group consisting of *Erwinia amylovora*, *Xanthomonas vesicatoria* and *Pseudomonas syringae*.

21. A method according to claim 19, wherein the plants are selected from the group consisting of fruit trees, horticultural trees and ornamental plants.

22. A method according to claim 19, wherein the composition is placed in contact with the soil, any growth medium which surrounds the roots of the plants, or parts of the plants selected from the group consisting of seeds, roots, stems, leaves or fruits.

23. A method according to claim 19, wherein the phytosanitary composition is placed in contact with the plant by spraying, immersion or watering.

* * * * *

SEQUENCE LISTING

<160> NUMBER OF SEQ ID NOS: 25

<210> SEQ ID NO 1
<211> LENGTH: 11
<212> TYPE: PRT
<213> ORGANISM: Artificial Sequence -continued

```
<220> FEATURE:
<223> OTHER INFORMATION: Synthetic Peptide

<400> SEQUENCE: 1

Lys Lys Leu Phe Lys Lys Ile Leu Lys Lys Leu
1               5                   10

<210> SEQ ID NO 2
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 2

Tyr Lys Leu Phe Lys Lys Ile Leu Lys Lys Leu
1               5                   10

<210> SEQ ID NO 3
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 3

Leu Lys Leu Phe Lys Lys Ile Leu Lys Lys Leu
1               5                   10

<210> SEQ ID NO 4
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 4

Phe Lys Leu Phe Lys Lys Ile Leu Lys Lys Leu
1               5                   10

<210> SEQ ID NO 5
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 5

Trp Lys Leu Phe Lys Lys Ile Leu Lys Lys Leu
1               5                   10

<210> SEQ ID NO 6
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 6

Lys Lys Leu Phe Lys Lys Ile Leu Lys Tyr Leu
1               5                   10

<210> SEQ ID NO 7
<211> LENGTH: 11
<212> TYPE: PRT
<213> ORGANISM: Artificial Sequence
<220> FEATURE:
<223> OTHER INFORMATION: Synthetic Peptide
```

```
<400> SEQUENCE: 7

Tyr Lys Leu Phe Lys Lys Ile Leu Lys Tyr Leu
1               5                   10

<210> SEQ ID NO 8
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 8

Leu Lys Leu Phe Lys Lys Ile Leu Lys Tyr Leu
1               5                   10

<210> SEQ ID NO 9
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 9

Phe Lys Leu Phe Lys Lys Ile Leu Lys Tyr Leu
1               5                   10

<210> SEQ ID NO 10
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 10

Trp Lys Leu Phe Lys Lys Ile Leu Lys Tyr Leu
1               5                   10

<210> SEQ ID NO 11
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 11

Lys Lys Leu Phe Lys Lys Ile Leu Lys Val Leu
1               5                   10

<210> SEQ ID NO 12
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 12

Tyr Lys Leu Phe Lys Lys Ile Leu Lys Val Leu
1               5                   10

<210> SEQ ID NO 13
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 13
```

```
Leu Lys Leu Phe Lys Lys Ile Leu Lys Val Leu
1               5                   10

<210> SEQ ID NO 14
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 14

Phe Lys Leu Phe Lys Lys Ile Leu Lys Val Leu
1               5                   10

<210> SEQ ID NO 15
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 15

Trp Lys Leu Phe Lys Lys Ile Leu Lys Val Leu
1               5                   10

<210> SEQ ID NO 16
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 16

Lys Lys Leu Phe Lys Lys Ile Leu Lys Phe Leu
1               5                   10

<210> SEQ ID NO 17
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 17

Tyr Lys Leu Phe Lys Lys Ile Leu Lys Phe Leu
1               5                   10

<210> SEQ ID NO 18
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 18

Leu Lys Leu Phe Lys Lys Ile Leu Lys Phe Leu
1               5                   10

<210> SEQ ID NO 19
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 19

Phe Lys Leu Phe Lys Lys Ile Leu Lys Phe Leu
```

```
1               5                   10
```

<210> SEQ ID NO 20
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 20

```
Trp Lys Leu Phe Lys Lys Ile Leu Lys Phe Leu
1               5                   10
```

<210> SEQ ID NO 21
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 21

```
Lys Lys Leu Phe Lys Lys Ile Leu Lys Trp Leu
1               5                   10
```

<210> SEQ ID NO 22
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 22

```
Tyr Lys Leu Phe Lys Lys Ile Leu Lys Trp Leu
1               5                   10
```

<210> SEQ ID NO 23
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 23

```
Leu Lys Leu Phe Lys Lys Ile Leu Lys Trp Leu
1               5                   10
```

<210> SEQ ID NO 24
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 24

```
Phe Lys Leu Phe Lys Lys Ile Leu Lys Trp Leu
1               5                   10
```

<210> SEQ ID NO 25
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 25

```
Trp Lys Leu Phe Lys Lys Ile Leu Lys Trp Leu
1               5                   10
```